United States Patent [19]

Kimura

[11] 4,266,549
[45] May 12, 1981

[54] LASER SCALPEL

[76] Inventor: Hiroaki Kimura, 57-69, Yamaquchi, Tokowzawa-shi, Saitama-ken, Japan

[21] Appl. No.: 31,209

[22] Filed: Apr. 18, 1979

[30] Foreign Application Priority Data

Oct. 12, 1978 [JP] Japan ............................. 53-124589

[51] Int. Cl.$^3$ ........................... A61B 6/08; A61N 5/06
[52] U.S. Cl. ................... 128/303.1; 128/395; 128/654; 128/665
[58] Field of Search ............ 128/630, 303.1, 395, 128/634, 664, 665, 654

[56] References Cited

U.S. PATENT DOCUMENTS

| | | | |
|---|---|---|---|
| 3,843,865 | 10/1974 | Nath | 128/395 |
| 3,865,113 | 2/1975 | Sharon et al. | 128/303.1 |
| 4,126,136 | 11/1978 | Auth et al. | 128/303.1 |
| 4,143,660 | 3/1979 | Malyshev et al. | 128/303.1 |
| 4,178,917 | 12/1979 | Shapiro | 128/665 |

OTHER PUBLICATIONS

Meyer et al.; A Laser Stimulator for the Study of Cutaneous Thermal Pain Sensations; 1/76, IEE Trans. on Biomed Engin., vol. BME-23, No. 1, pp. 54–60.
Porphyrins, by A. Vannotti, Hilger & Watts, Ltd., London, 1954, pp. 18, 19, 24, 25, 72 & 73.

*Primary Examiner*—Robert W. Michell
*Assistant Examiner*—Arthur S. Rose

[57] ABSTRACT

Disclosed herein is a laser scalpel which uses a krypton beam or a ray of light projected from a mercury lamp having a wave-length in the range of 3,950–4,200Å as a guide light converging at the focal point or in the vicinity of the focal point of a laser beam for a surgical operation, for indicating focal point of said laser beam, which is equipped on its manipulator with a radiation detector or detectors enabling the detection of hematoporphyrin or isotopes built up in advance in the site of a tumor at said focus or in the vicinity thereof and to thus detect the tumor site at the time of irradiation of said laser beam for surgical operation and which makes it possible to simultaneously perform both diagnosis and treatment of the tumor.

5 Claims, 8 Drawing Figures

LASER SCALPEL

BACKGROUND OF THE INVENTION

This invention relates to a laser scalpel capable of performing simultaneously both diagnosis and treatment of the site of a tumor.

In the surgical removal of a malignant tumor, a surgeon makes strenuous efforts to completely remove the tumor. If even a minute portion of the malignant tumor is left, the tumor will regenerate from the residual site and transfer to another part of the body. The diagnosis of the site of the tumor or its boundary has so far been made empirically by touch or by the visual confirmation of the surgeon. However, it has been extremely difficult to perfectly solve the problem of the remaining site of the tumor.

On the other hand, a laser scalpel has been used for the treatment of tumors by concentrating a $CO_2$ laser beam, a YAG laser beam, etc. at one point, bombarding the tumor with photons at a massive power density and thus burning up and evaporating the tumor. However, the laser beam for a surgical operation of this kind is invisible to the human eye and is dangerous if used as it is. Accordingly, a method has been used in which the focal point, or the vicinity of the focal point, of the laser beam is irradiated with a guide light so that the surgeon can confirm the focal point and ensure a smooth operation.

OBJECTS

The first object of the present invention is therefore directed to provide a laser scalpel which makes it possible to perform simultaneously both operation and diagnosis of a tumor by furnishing the guide light with a tumor site detection function in addition to the abovementioned indication function. To accomplish this object, the present invention uses as the guide light visible light having a wavelength of 3,950–4,200 Å, specifically a krypton laser beam or a beam projected from a mercury lamp. On the other hand, hemataporphyrin derivatives of the following formula are built up in advance by an intraveneous injection at the site of the tumor of the living body which is to be the subject of the surgical operation or diagnosis:

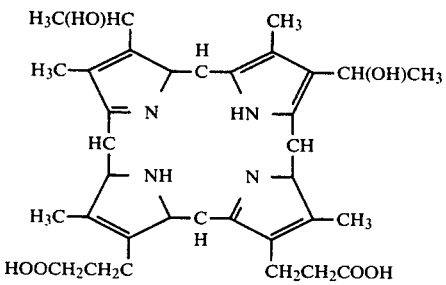

These derivatives are responsive to the abovementioned specific visible light and generate red flurorescence at the site of the tumor. As a result, the surgeon is able to confirm the tumor site by means of this red fluorescence and perfectly remove the tumor without leaving any trace behind.

The second object of the present invention is to provide a laser scalpel which irradiates visible light of a wavelength of 3,950–4,200 Å as the guide light for the surgical operation laser beam and which is equipped, at the tip portion of a manipulator of the laser scalpel, with a radiation detector directed toward the laser beam focal point and its vicinity. The radiation emitted from the tumor site at the laser beam focal point and the vicinity thereof are incident upon this radiation detector. Radioisotopes such as $^{67}$Ga-citrate, $^{51}$Co-bleomycin and the like accumulate in advance at the tumor site due to the intraveneous injection.

The third object of the present invention is to provide a laser scalpel which irradiates visible light of a wavelength of 3,950–4,200 Å as the guide light of the operation laser beam and which is equipped with an adaptor implanted in the tip portion of its manipulator so as to extend in the advancing direction of the beam. This adaptor keeps constant the distance between the tip of the manipulator and the irradiation surface, and a throughhole is bored through the inner wall at the tip portion of the adaptor so as to communicate with its outer wall so that the smoke generated at the time of a surgical operation is discharged to the outside by means of a suction device.

BRIEF DESCRIPTION OF THE DRAWINGS

Other objects of the present invention will become more apparent from the following detailed description.

Referring now to the accompanying drawings,

FIG. 3 is a perspective view of FIG. 2;

FIGS. 4A, B and C are sectional views showing a variety of shapes of the tip of the radiation detector;

DESCRIPTION OF THE PREFERRED EMBODIMENTS

An important feature of the laser scalpel in accordance with the present invention is the use, as a guide light, of visible light having a wavelength of 3,950–4,200 Å, especially a krypton laser beam and a light beam projected from a mercury lamp.

Though the krypton laser beam oscillates at various wavelengths ranging from the ultraviolet range to the infrared range, the present invention specifically uses the three violet wavelengths of 4,154 Å, 4,131 Å and 4,067 Å. These beams are used as the guide light indicating the focal point and the vicinity of the focus of the surgical operation laser beam. Since the light of the mercury lamp is natural light, a filter is ordinarily necessary for picking up the visible light in the range of 3,950–4,200 Å.

Figure 1:
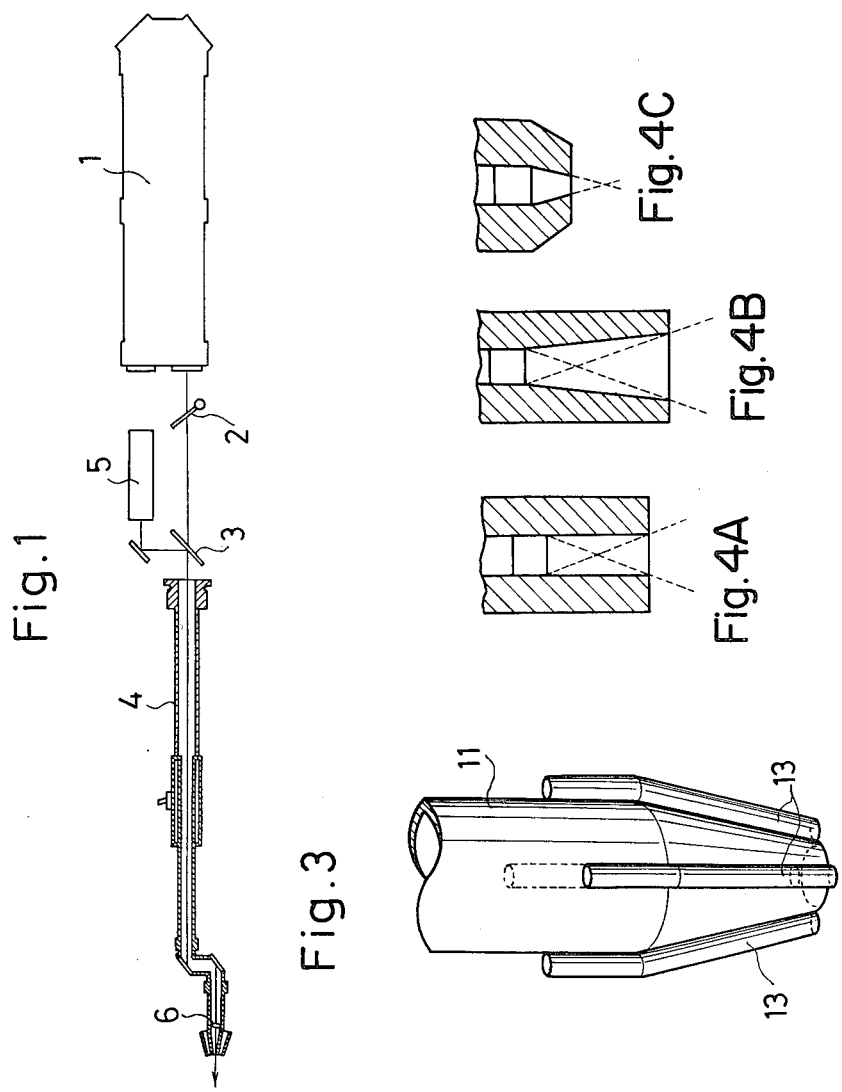
FIG. 1 is a schematic view of an embodiment of the laser scalpel in accordance with the present invention wherein the surgical operation laser beam and the guide light are shown advanced coaxially with each other.

Turning now to FIG. 1 which shows an embodiment of the present invention, the surgical operation laser beam oscillated by an operation beam oscillator 1 enters the manipulator 4 of the laser scalpel through a beam shutter 2 and a mixing filter 3. At the same time, the visible light in accordance with the present invention, which is irradiated from a light source 5, reflects off the surface of the mixing filter 3, is caused to advance coaxially with the surgical operation laser beam and is condensed together with the surgical operation laser beam by a lens 6 incorporated in the manipulator 4. They are then emitted from the top of the manipulator and irradiate the living body so that the focal point of the surgical operation laser beam is in conformity with that of the visible light. As a result, the surgeon is allowed to confirm the converging position of the surgical operation laser beam.

Recent studies have revealed that when the hemataporphyrin derivatives are supplied to the living body by the intraveneous injection, they accumulate in the cancerous cells but not in the normal cells, and especially in large quantities in foci such as lung cancer. However, these derivatives are excited by the visible light of the wavelength of 3,950–4,200 Å and generate red fluorescence of 6,250–7,000 Å.

The inventor of the present invention has found that when the abovementioned visible light, especially the krypton laser beam or the light projected from a mercury lamp, is used to irradiate the tumor site at which the hemataporphyrin derivatives are accumulated, red fluorescence is confirmed visibly at the irradiated site.

For the abovementioned reason, these visible rays of light not only exhibit the function of the guide light enabling the visual observation of the converging position of the surgical operation laser beam but also make it possible to make a diagnosis of the site of the tumor. The present invention has been perfected on the basis of this conception.

As the tumor site can be confirmed by the visible light as the guide light, the laser scalpel in accordance with the present invention projects the operation laser beam onto the site of the tumor by opening a foot switch, etc. immediately after confirmation, and thus makes the necessary treatment. Since this operation can be repeated from the surface of the living body, it is possible to perfectly remove the site of the tumor.

Red fluorescence due to irradiation of the visible light in accordance with the present invention can be confirmed not only visually but also by other means. For example, the light may be detected by use of a filter allowing the passage therethrough of only a red light so as to convert the light so detected into an electric signal for the purpose of electrical confirmation.

Figure 2:
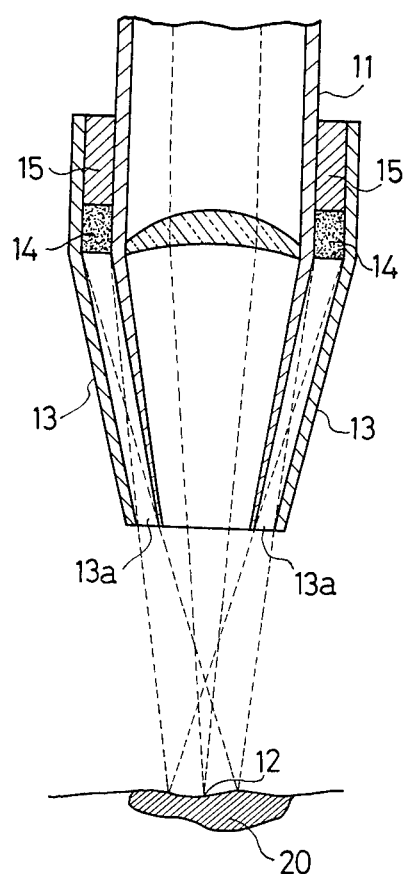
FIG. 2 is a sectional view of the laser scalpel wherein the radiation detector in accordance with the present invention is shown fitted to the tip of the manipulator.

FIG. 2 shows the tip portion of the manipulator of the laser scalpel which is additionally equipped with the radiation detector capable of capturing the radiation emitted from the tumor site to thus confirm the site. The shell 11 of the manipulator has a tapered tip and the surgical operation laser beam as well as the guide light are converged on the focal point 12 and its vicinity. As shown in FIG. 3, the radiation detector 13 in accordance with the present invention is directed toward the focal point 12 by means of a plurality of collimators adapted to the outside of the manipulator. The shells of these collimators are preferably made from materials prohibiting the passage of the radiation therethrough, especially metals such as lead, gold and tungsten each incorporating a few percent of antimony or bismuth to obtain suitable hardness, or mercury sealed in a glass vessel. Among these materials, a material as light as possible is selected for the easy handling of the scalpel by the surgeon. A eutectic crystal 14 such as NaI(Tl) is sealed in the shell so as emit light in response to the incident radioactive rays through the aperture 13a at the tip of the detector. Adjacent this crystal, there is embedded a photoelectric conversion element 15 to convert the emitted light into an electric signal, of which the current is amplified by an amplifier and converted to an audible sound for detection through a speaker that is not shown. A photomultiplier may be used instead of the photoelectric conversion element.

As shown in FIG. 3, plural radioactive detectors are ordinarily fitted to the tip of the manipulator and collect the radiation emitted from the tumor site that occupies a predetermined area with the focal point of the laser beam as its center. If these detectors are arranged such that the speaker is not actuated when only a part of the detectors respond to the radiation but is actuated only when all the detectors respond, the focal point of the laser beam can be located immediately above the tumor site, thereby enabling the optimum locationing of the scalpel on the irradiation surface.

Instead of the abovementioned method of confirmation of the tumor site by sound, the confirmation may be made by picture or graphic representation. In other worde, it is possible to display the site as a picture or a CRT by proper combination of the detectors, photomultipliers, position-counting circuits and the like or to display the position of the site in section as a graph on the CRT.

Next, the radioactive rays emitted from the tumor site will be explained. It is known that if radioisotopes such as $^{67}$Ga-citrate or $^{51}$Co-bleomycin are injected intraveneously into a living accumulation being specifically remarkable at the site of a malignant lymph tumor or that of a lung cancer. Accordingly, the site of a tumor can be confirmed by capturing the radiation irradiated while the abovementioned isotopes accumulate due to the intraveneous injection, and can be diagnosed more reliably by the joint use of the aforementioned guide light. Hence, surgery to be carried out simultaneously can be applied all the more suitably.

The tip portion of the detector upon which the radiation is incident is not specifically limited to the straight type used in the abovementioned embodiment and shown in FIG. 4(A). Namely, the flat field type such as shown in FIG. 4(B) or the tapered type in FIG. 4(C) may also be used. These types are properly selected in accordance with the kind of tumors, the size of the site, the required sensitivity and similar factors.

Figure 5:
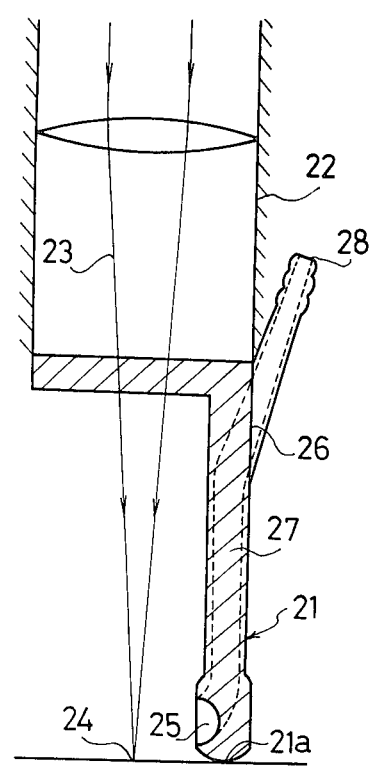
FIG. 5 is a sectional view of the adaptor in accordance with the present invention.

FIG. 5 shows further the laser scalpel in accordance with the present invention which is equipped with a specific adaptor 21 at the tip of the manipulator 22. This adaptor 21 is implanted in the tip of the manipulator 22 to extend in the advancing direction of the laser beam 23 and keeps the manipulator 22 at a predetermined height from the irradiation surface 24. The entire part or at least its tip portion 21a of the adaptor is made of an insulating material and the tip portion 21a is rounded in order to facilitate sliding on the irradiation surface 24.

A smoke suction port 25 is defined on the inner wall of the adaptor 21 while a smoke discharge port 26 is defined on the outer wall. These two ports are communicated with each other by a through-hole 27. Two or more through-holes 27 may also be formed, if necessary. A nose section 28 is formed protrusively from the smoke discharge port 26a for connection with a compulsive suction device via a rubber hose.

Usually the height of the adaptor is set to keep the manipulator at such a level that the focal point of the beam is in conformity with the surface of the living body. In the case of the out-of-focal state where the focus is placed slightly above the surface of the living body or inside the living body in accordance with the necessity of the operation, the manipulator may have such a construction that enables optional adjustment of its height. In accordance with this adaptor, it is possible to discharge rapidly and reliably the smoke generated in large quantities due to burning and evaporation of the living tissue by means of the suction device connected to the nose section, so that the laser scalpel is free from the problem of malodorous smoke which would otherwise disturb the sight of the surgeon and be inhaled by the surgeon.

Figure 6A:
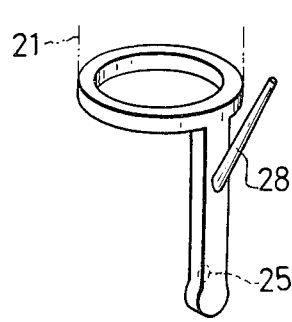
FIGS. 6a, 6b and 6c are perspective views showing a variety of embodiments of the adaptor.
Figures 6B, 6C:
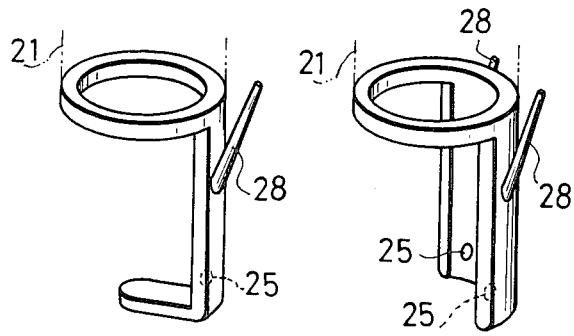

FIG. 6 shows adaptors each having various shapes. FIG. 6(a) shows the adaptor having a rod-like shape, FIG. 6(b) one having its tip bent in a spatula-like shape and FIG. 6(c) one having two through-holes.

What is claimed is:

1. In a laser scalpel comprising a laser beam generator capable of generating energy sufficient to vaporize human tissue, a laser beam manipulator having a laser beam entrance end and a laser beam emitting end, a mixing filter, said laser beam generator and said mixing filter being arranged such that the laser beam from said generator is directed through said mixing filter and into said entrance end, a beam shutter positioned such that it may interrupt said laser beam when desired, a guide light source arranged such that the light from said source is directed through said mixing filter into said entrance end whereby during use of said scalpel said guide light is irradiated onto approximately the focal point of the laser beam emitted from said manipulator emitting end, the improvement which comprises:

said guide light emits substantially only light having wavelengths between about 3,950 to 4,200 Å, a radiation detector fitted upon said laser beam emitting end of said manipulator capable of capturing radiation emitted from a surface located approximately at said focal point of said laser beam, said detector being responsive only to light within a wavelength range different from the wavelength of said guide light, and means to convert radiation captured by said detector into an electric signal.

2. A laser scalpel of claim 1 having means fitted to said laser beam emitting end for removing smoke generated by said laser beam from the region of the smoke generation.

3. A laser scalpel of claim 1 wherein said guide light is projected from a mercury vapor lamp.

4. A laser scalpel of claim 1 wherein said guide light is projected from a Krypton laser.

5. A laser scalpel of claim 1 wherein a plurality of said radiation detectors are fitted upon said laser beam emitting end.

* * * * *